United States Patent [19]

Bell

[11] 4,303,661
[45] Dec. 1, 1981

[54] BENZYL-TETRAHYDRO-2,4-DIHYDROXY-1,6-NAPHTHYRIDINE-3 CARBOXYLIC ACID TYPE ANTIALLERGY AGENTS

[75] Inventor: Stanley C. Bell, Narberth, Pa.

[73] Assignee: American Home Products Corporation, New York, N.Y.

[21] Appl. No.: 197,843

[22] Filed: Oct. 17, 1980

[51] Int. Cl.³ .................. A61K 31/495; C07D 471/04
[52] U.S. Cl. .................................... 424/256; 546/123
[58] Field of Search ......................... 546/123; 424/256

[56] References Cited

PUBLICATIONS

Yamamoto et al., Heterocycles, vol. 11 (1978) pp. 267–273.

Primary Examiner—Henry R. Jiles
Assistant Examiner—Bernard Dentz
Attorney, Agent, or Firm—Richard K. Jackson

[57] ABSTRACT 1,6-Naphthyridine derivatives of the formula:

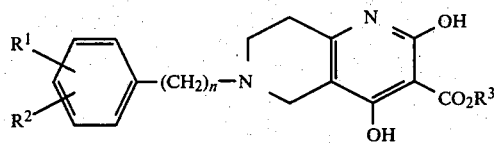

in which
$R^1$ and $R^2$ are, independently, hydrogen, alkyl of 1 to 3 carbon atoms, halo, or trifluoromethyl;
$R^3$ is hydrogen, alkyl of 1 to 6 carbon atoms or a pharmaceutically acceptable metal or amine cation; and
n is one of the integers 1, 2 or 3;

or a pharmaceutically acceptable salt thereof and pharmaceutical compositions containing those compounds are useful as antiallergy agents effective prophylactically to relieve the symptoms manifest in atopic immediate sensitivity in mammals.

12 Claims, No Drawings

BENZYL-TETRAHYDRO-2,4-DIHYDROXY-1,6-NAPHTHYRIDINE-3 CARBOXYLIC ACID TYPE ANTIALLERGY AGENTS

BACKGROUND OF THE INVENTION

Atopic immediate sensitivity is the chief manifestation found in animals suffering from bronchial asthma, seasonal pollinosis (e.g. hay fever), allergic rhinitis, urticaria, allergic conjunctivitis, food allergies and anaphylactoid reactions. The substances most frequently responsible for clinically manifest sensitivities are plant pollen, animal feathers and danders, dust milk and wheat, whether inhaled or ingested. Atopic hypersensitivity is found in man, dog and other animals. Its occurence is exceptionally found in the lower animals.

The presence of antibodies associated with atopic hypersensitivity reactions in the host serum is established by the passive sensitization of the skin of a normal recipient, after injection of serum from a sensitized host into a skin site followed by injection of antigen into the same area 24 hours later, resulting in a local hive. This is commonly referred to as the Prausnitz-Kustner (P-K) reaction.

The antibody associated with atopic hypersensitivity possesses distinctive features in that it does not in all forms precipitate with its antigen, fails to pass the placenta from mother to fetus, has special affinity for the skin, frequently lacks specificity toward an individual antigenic factor and is usually labile at about 56° C. after 2 hours.

The homocytotropic antibody found in or induced in the rat is related in function and reaction to immunoglobulin E (reagin or IgE) found in the human. The correlation between homocytotropic antibody in the rat and IgE in the human has been established through the common effects obtained from chemical reactions, immunological reactions and drug responses in the two species hosting those antibodies. In the human, reagin is the antibody responsible for atopic immediate hypersensitivity reactions. In the rat, the homocytotropic antibody is responsible for atopic immediate hypersensitive reactions.

In theory, reagin, influences the cell membrane of a mast cell by reacting with an antigen, to initiate the reaction(s) within the mast cell which ultimately releases a mediator such as Bradykinin, SRS-A (slow reacting substance-A), histamine and other unknown substances. The mediator effects a change in surrounding cell wall permeability permitting a rapid change in flow or exudance of mediator(s) from the cells, resulting in an allergic attack symptom. The various methods commonly employed to relieve the symptoms of allergic attack, none of which are considered to be quite acceptable, are to (1) avoid attack by the antigen, (2) block the production of antibody with an immuno-suppressant, (3) block the action of the mediators on the cell under attack by administration of anti-histaminics, anti-5-hydroxy-tryptamines (5-HT) or anti-inflammatories, or (4) stimulate the cell under attack to negate the action of the mediator through the action of bronchodilators such as Isoprel ® or a xanthine.

DESCRIPTION OF THE INVENTION

In accordance with this invention, there is provided a group of novel antiallergy agents, certain pharmaceutical compositions and a method for prophylactically treating a sensitized mammal with the active antiallergic agent of those compositions to prevent the symptoms manifest in an immediate hypersensitivity reaction between reaginic type antibodies and an antigen which comprises administering to said mammal an effective amount of a compound of the formula:

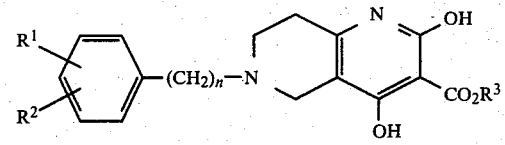

in which $R^1$ and $R^2$ are, independently, hydrogen, alkyl of 1 to 3 carbon atoms, halo or trifluoromethyl;

$R^3$ is hydrogen, alkyl of 1 to 6 carbon atoms or a pharmaceutically acceptable metal or amine cation and n is one of the integers 1, 2 or 3.

The novel antiallergy agents are of the formula:

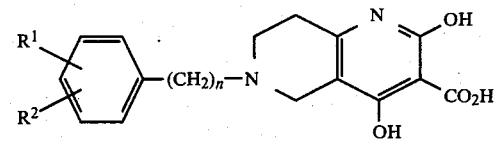

where $R^1$ and $R^2$ are, independently, hydrogen, alkyl of 1 to 3 carbon atoms, halo or trifluoromethyl; and n is one of the integers 1, 2 or 3 or a pharmaceutically acceptable salt thereof. The preferred antiallergy agents are those in which n is 1.

These compounds are prepared by conventional procedures from the corresponding esters which are either known compounds or are routinely prepared. For example, 6-benzyl-5,6,7,8-tetrahydro-2,4-dihydroxy-1,6-naphthyridine-3-carboxylic acid, ethyl ester is disclosed in a tautomeric form in Heterocycles 11 267–273 (1978) as compound 4a. Conversion of the esters to the free acid or desired salt is effected by known mild reaction conditions.

The preferred pharmaceutical compositions for use in the method of this invention, are those embraced by the preceding structural formula where n is 1, represented by the formula:

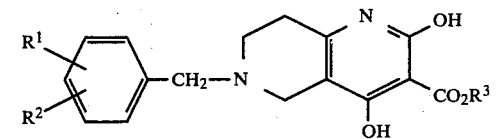

in which $R^1$ and $R^2$ are, independently, hydrogen, alkyl of 1 to 3 carbon atoms, halo or trifluoromethyl; and $R^3$ is hydrogen, alkyl of 1 to 6 carbon atoms or a pharmaceutically acceptable metal or amine cation; and a pharmaceutical carrier.

The antiallergy agents employed in the compositions and method aspects of this invention may appear as tautomers such as follows:

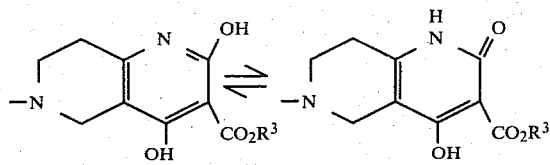

and it is intended that depiction of one tautomer throughout the specification and appended claims will embrace the other tautomers.

The pharmaceutically acceptable metal or amine salts include such metal salts as the alkali metal, e.g., lithium, sodium, and potassium; the alkaline earth metals, e.g., magnesium and calcium; aluminum, zinc; and the like. Various amines are those derived from primary, secondary or tertiary amines, such as methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine and like aliphatic, cycloaliphatic, and araliphatic amines containing up to and including about eighteen carbon atoms as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, and the like as well as amines containing hydrophilic groups, e.g., mono-, di-, and triethanolamine, ethyldiethanolamine, N-butylethanolamine, 2-amino-1-butanol, 2-amino-1-ethyl-1,3-propanediol, 2-amino-2-methyl-1-propanol, tris(hydroxymethyl)aminomethane, phenylethanolamine, glactamine, N-methylglucamine, N-methylglucosamine, procaine, and the like. Similarly applicable are the quaternary ammonium, tetramethylammonium, tetraethylammonium, benzyltrimethylammonium, phenyltriethylammonium salts.

Although the compounds described above may be administered neat or in pure form, depending upon the route of administration, whether oral, or parenteral, it is most desireable that they be formulated in conventional manner for pharmaceutical composition delivery. Such pharmaceutical compositions in unit dosage forms include solids (e.g., tablets or capsules) or liquids (e.g., sterile parenteral solutions or suspensions) containing an effective amount of the antiallergy agent of this invention.

Tablets and capsules contain the active antiallergy agent in combination with conventional ingredients such as starch, lactose, methylcellulose, magnesium stearate, dicalcium phosphate, magnesium aluminum silicate, or similar carriers.

Liquid dosage formulations for parenteral administration are preferably prepared as sterile, aqueous isotonic solutions with or without conventional adjuvants such as buffering, surfactant and/or preserving agents.

For use as an inhalant or for intranasal administration either a micropulverised powder, aqueous solution or suspension for use in a nebulizer or a pressurized aerosol may be employed conventionally.

EXAMPLE 1

Tablets are compressed from a mixture of 1,000 parts 6-benzyl-5,6,7,8-tetrahydro-2,4-dihydroxy-1,6naphthyridine-3-carboxylic acid ethyl ester; 100 parts dicalcium phosphate; 60 parts methylcellulose (7.5 percent aqueous solution) for granulation of the above two ingredients; 150 parts talc; 200 parts cornstarch and 10 parts magnesium stearate.

EXAMPLE 2

A sterile aqueous solution for parenteral administration is prepared by dissolving 10 milligrams of 6-benzyl-5,6,7,8-tetrahydro-2,4-dihydroxy-1,6-naphthyridine-3-carboxylic acid, triethylamine salt and sufficient sodium chloride to afford an isotonic solution.

The antiallergy agents disclosed herein may advantageously be administered in conjunction with known compounds effecting anti-histaminic, anti-hypertensive, analgesic, central nervous system depressant, immunosuppressive, anti-serotonin, anti-Bradykinin or endocrinological responses.

Thus, there is provided herewith a method for suppressing allergic manifestations of atopic immediate sensitivity in warm-blooded human and non-human animals, the latter including domesticated animals such as the mouse, rat, hamster, gerbil, dog, cat sheep, goat, horse, cow, and the like, by administering an effective amount of one or more of the compounds disclosed in this application by oral, topical, intraperitoneal, intramuscular or intravenous routes.

The technique employed to establish the anti-allergic activity of the disclosed compounds is reported in Immunology, vol. 16 pp. 749–760 (1969) and involves four male Charles River rats (200–250 grams body weight) per group to provide a control, a host for administration of a standard anti-allergic compound (disodium cromoglycate) and animals for the test compound. The rats were injected intracutaneously on their shaved backs with sera from rats immunized with egg albumin and pertussis vaccine. Twenty-four hours after the initial injections, the test compound was administered orally at a dosage level of 25 milligrams per kilogram host body weight. Sixty minutes later 1 milliliter of a 0.5 percent solution of Evans blue dye and 8 milligrams of egg albumin is injected intravenously. After 30 minutes, the animal is sacrificed and the bleb size on its back is measured. The mean bleb size for the animals administered the test compound is calculated and the percent inhibition is determined by comparison with the control animal.

Following that procedure, 6-benzyl-5,6,7,8-tetrahydro-2,4-dihydroxy-1,6-naphthyridine-3-carboxylic acid ethyl ester, representative of the other compounds disclosed herein, afforded 62 percent inhibition of the skin reaction developed in the control animals. Following the same protocal with a 10 milligrams per kilogram dose resulted in 26.1 percent inhibition ($p < 0.05$).

Although the mechanism by which the compounds of this invention function is not absolutely known, applicant has found that the disclosed compounds, in a manner believed to be similar to the function of INTAL ®, block reaction(s) in the mast cell leading to the production and release of mediators. The compounds of this invention permit the occurrence of a non-productive antigen-antibody interaction. They effectively block the IgE type reaction.

In essence, the compounds of this invention block the release of mediators commonly resulting from the antigen-antibody reaction as exemplified in a passive cutaneous anaphylaxis test (PCA) using rat homocytotropic antibody—a known correlate of human reaginic antibody.

By analogy to disodium cromoglycate and its activity correlation between standard test animals, domestic animals and man, the compounds of this invention have been established as anti-allergic agents suitable for the same uses at analogous doses and through the same routes of administration as INTAL ®.

The effective dose to be employed will vary with the compound administered, the route of administration, specific condition of the patient and the desired degree of relief sought. The oral dose will generally lie in the range from about 1 milligram to 100 milligrams per kilogram body weight, to be given optionally in divided doses two to four times daily, to achieve that level of symptomatic relief desired.

What is claimed is:

1. A compound of the formula:

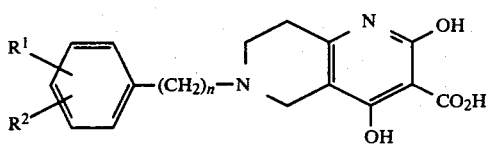

in which
$R^1$ and $R^2$ are, independently, hydrogen, alkyl of 1 to 3 carbon atoms, halo or trifluoromethyl; and
n is one of the integers 1, 2 or 3;
or a pharmaceutically acceptable salt thereof.

2. A compound of claim 1 of the formula:

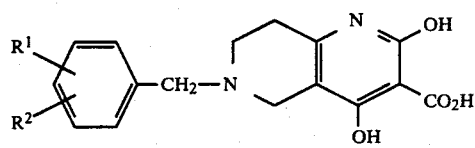

in which $R^1$ and $R^2$ are, independently, hydrogen, alkyl of 1 to 3 carbon atoms, halo or trifluoromethyl; or a pharmaceutically acceptable salt thereof.

3. The compound of claim 2 which is 6-benzyl-5,6,7,8-tetrahydro-2,4-dihydroxy-1,6-naphthyridine-3-carboxylic acid or a pharmaceutically acceptable salt thereof.

4. A pharmaceutical composition which comprises an antiallergic amount of a compound of the formula:

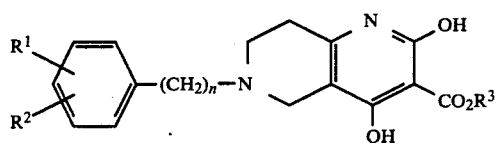

in which
$R^1$ and $R^2$ are, independently, hydrogen, alkyl of 1 to 3 carbon atoms, halo or trifluoromethyl;
$R^3$ is hydrogen, alkyl of 1 to 6 carbon atoms or a pharmaceutically acceptable metal or amine cation and
n is one of the integers 1, 2 or 3
and a pharmaceutical carrier.

5. A composition of claim 4 in which n is 1.

6. A composition of claim 4 in which said carrier is liquid

7. A composition of claim 6 in which said liquid is aqueous.

8. A composition of claim 4 in which said carrier is solid.

9. A method for prophylactically treating a sensitized mammal to prevent the symptoms manifest in an immediate hypersensitivity reaction between reaginic type antibodies and an antigen which comprises administering to said mammal an effective amount of a compound of the fomrula:

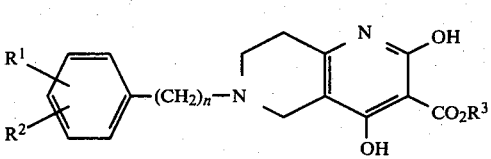

in which
$R^1$ and $R^2$ are, independently, hydrogen, alkyl of 1 to 3 carbon atoms, halo, or trifluoromethyl;
$R^3$ is hydrogen, alkyl of 1 to 6 carbon atoms or a pharmaceutically acceptable metal or amine cation; and
n is one of the integers 1, 2 or 3; and a pharmaceutical carrier.

10. The method of claim 9 which comprises administering to said sensitive mammal a compound of the formula:

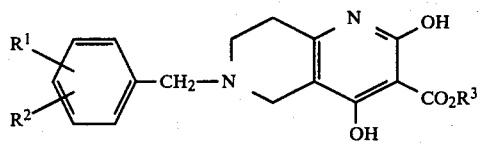

in which
$R^1$ and $R^2$ are, independently, hydrogen, alkyl of 1 to 3 carbon atoms, halo or trifluoromethyl; and
$R^3$ is hydrogen, alkyl of 1 to 6 carbon atoms;
or a pharmaceutically acceptable metal or amine cation.

11. The method of claim 9 in which the compound administered is 6-benzyl-5,6,7,8-tetrahydro-2,4-dihydroxy-1,6-naphthyridine-3-carboxylic acid ethyl ester.

12. The method of claim 9 in which the compound administered is 6-benzyl-5,6,7,8-tetrahydro-2,4-dihydroxy-1,6-naphthyridine-3-carboxylic acid or a pharmaceutically acceptable salt thereof.

* * * * *